US00PP27574P3

(12) United States Plant Patent
Olesen

(10) Patent No.: US PP27,574 P3
(45) Date of Patent: Jan. 24, 2017

(54) GROUND COVER ROSE PLANT NAMED 'POULTC021'

(50) Latin Name: ***Rosa* hybrid**
Varietal Denomination: Poultc021

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 120 days.

(21) Appl. No.: 14/121,268

(22) Filed: Aug. 15, 2014

(65) Prior Publication Data

US 2016/0050815 P1 Feb. 18, 2016

(51) Int. Cl.
*A01H 5/02* (2006.01)

(52) U.S. Cl.
USPC ..... Plt./101

(58) Field of Classification Search
USPC ..... Plt./101, 102
See application file for complete search history.

(56) References Cited

PUBLICATIONS

Poulsen Roser A/S—"Pagode-Perfection by Poulsen," Main Varieties 2013, retrieved off the internet Feb. 3, 2016 (1 page).*

* cited by examiner

*Primary Examiner* — Susan McCormick Ewoldt

(57) ABSTRACT

A new garden rose plant of the Ground Cover class which has abundant, orange flowers and attractive foliage. This new and distinct variety has shown to be uniform and stable in the resulting generations from asexual propagation.

1 Drawing Sheet

Botanical designation: *Rosa* hybrid.

Variety denomination: 'Poultc021'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2006 and the resulting seeds were planted in a controlled environment in Fredensborg, Denmark. The new variety, named 'Poultc021', originated as a single seedling from the stated cross.

The new variety may be distinguished from its male pollen parent and female seed parent by the following characteristics. The female seed parent has medium yellow flowers while the new variety has orange flowers. The male pollen parent has orange red flowers.

The objective of the hybridization of this rose variety was to create a new and distinct variety for garden use with unique qualities, such as:

1. Uniform and abundant orange flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poultc021' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poultc021' was selected in the spring of 2007 by the inventor as a single plant from the progeny of the aforementioned hybridization.

Asexual reproduction of 'Poultc021' by traditional budding and rooted cuttings was first done by Mogens N. Olesen in the nursery in Fredensborg, Denmark in July, 2007. This initial and other subsequent asexual propagations conducted in controlled environments have demonstrated that the characteristics of 'Poultc021' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poultc021'. Specifically illustrated in the drawing are a flowering branch, flower in parts, leaves, and stems. Plants shown are 2 years of age.

DETAILED DESCRIPTION OF THE VARIETY

The following is a description of 'Poultc021', as observed in its growth in in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Chewmaytime', U.S. Plant Pat. No. 18,347 are compared to 'Poultc021' in Chart 1.

CHART 1

| | 'Poultc021' | 'Chewmaytime' |
|---|---|---|
| Petal Count | 20 | 5 |
| Flower Diameter | 45 mm | 48 mm |
| Petal color, upper surface after opening. | Orange-Red Group N30B splashed with Yellow Group 9B at the basal zone | Red 43C, becoming closer to 52D with development. |

FLOWER AND FLOWER BUD

Blooming habit: Continuous.

Flower bud:

*Size*.—Upon opening, 15 mm in length from base of receptacle to end of bud. Bud diameter is 10 mm.

*Bud form*.—Globose.

*Bud color*.—As sepals divide petals are Orange Group 24B with intonations of Orange-Red Group 33B.

*Sepal inner surface*.—Color: Green Group 138B. Surface: Lightly pubescent.

*Sepal outer surface*.—Color: Yellow-Green Group 144B with strong intonations of Greyed-Purple Group 183A. Texture: Smooth.

*Sepal shape*.—Apex: Cirrhose. Base: Flat at union with receptacle.

*Sepal margin*.—Margins have very weak foliaceous appendages on three of the five sepals.

*Sepal size*.—15 mm long, 5 mm wide.

*Receptacle*.—Texture: Smooth. Size: 5 mm in height, 6 mm wide. Color: Yellow-Green Group 144A with strong intonations of Greyed-Purple Group 183A. Shape: Globose.

*Pedicel*.—Surface: Smooth. Length: About 25 mm. Diameter: 1 mm. Color: Yellow-Green Group 144B with strong intonations of Greyed-Purple Group 183A. Strength: Strong.

*Peduncle*.—Length: 20 to 30 mm. Diameter: 2.5 mm. Color: Yellow-Green Group 145B with intonations of Greyed-Purple Group 183D. Texture: Smooth.

Flower bud development: Flower buds are borne in clusters of 3 to 7 flower buds per stem.

Flower bloom:

*Fragrance*.—Moderate honey scent.

*Duration*.—The blooms have a duration on the plant of approximately 7 days. Petals fall cleanly away from plant after flowers have fully matured.

*Size*.—Flower diameter is 45 mm when open. Flower depth is 15 mm.

*Flower shape*.—Single, fully open exposing flower parts.

*Shape of flower, side view*.—The upper portion is flat. The lower portion is convex.

Petalage: Under normal conditions, flowers have 20 petals total, 1 or 2 of which are petaloids.

General tonality of flower: Open flowers are Orange-Red Group N30B.

Petal color:

*Upper surface*.—Orange-Red Group N30B splashed with Yellow Group 9B at the basal zone.

*Lower surface*.—Blend of Orange Group 28D and Orange-Red Group 31A. The basal zone is splashed with Yellow Group 9B.

Petals:

*Petal reflex*.—Flat.

*Margin*.—Entire and uniform. Moderate undulations.

*Shape*.—Generally rounded. Apex shape: Mucronate. Base shape: Broadly acute.

*Size*.—About 20 mm (l)×20 mm (w).

*Texture*.—Smooth.

*Thickness*.—Moderate.

Petaloids:

*Size*.—13 mm (l) by 10 mm (w).

*Shape*.—Acute apex with cleft, base is acute.

*Color*.—Upper surface: Orange-Red Group N30B splashed with Yellow Group 9B at the basal zone. Lower surface: Blend of Orange Group 28D and Orange-Red Group 31A. The basal zone is splashed with Yellow Group 9B.

Reproductive organs:

*Pollen*.—None observed.

*Anthers*.—Size: 1 mm in length. Color: Greyed-Orange Group 164A. Quantity: 60 on average.

*Filaments*.—Color: Yellow-Orange Group 20A. Length: 4 mm.

*Pistils*.—Length: 3 mm. Quantity: 15 on average.

*Stigmas*.—Color: Greyed-Yellow Group 162A.

*Styles*.—Color: Red-Purple Group 59A.

*Location of stigmas*.—Level location relative to the length of the filaments and the height of the anthers.

*Hips*.—None Observed.

PLANT

Plant growth: Upright, bushy. Plants are 30 cm in height, and 30 cm wide.

Stems:

*Color*.—Juvenile growth: Yellow-Green Group 145A with intonations of Greyed-Red Group 182B. Mature growth: Yellow-Green Group 145A.

*Length*.—On average, canes are 15 cm from the base of the plant to the flowering portion.

*Diameter*.—4 mm.

*Internodes*.—On mature canes, there is an average distance of 15 mm between nodes.

*Surface texture*.—Young wood: Smooth. Older wood: Smooth.

Long prickles:

*Incidence*.—10 prickles per 10 cm of stem.

*Size*.—Average length of prickles on mature stems is 6 mm.

*Shape*.—Upper and lower side are linear.

*Color*.—Juvenile prickles: Greyed-Purple Group 183C. Mature prickles: Greyed-Purple Group 183C.

Plant foliage:

*Compound leaf*.—65 mm (l)×35 (w).

*Quantity*.—4 leaves per 10 cm of stem on average.

*Leaf bearing angle to the stem*.—45 degrees.

*Color of juvenile foliage*.—Upper side: Yellow-Green Group 146A. Margins are Greyed-Purple Group 183A. Lower side: Yellow-Green Group 146B.

*Color of mature foliage*.—Upper side: Yellow-Green Group 146A. Lower side: Yellow-Green Group 146B.

Plant leaves and leaflets:

*Stipules*.—Size: 9 mm long, 3 mm wide. Quantity: 2 per compound leaf. Shape: Linear, slightly broad based with outward extending apices. Margins: Finely serrated. Color: Yellow-Green Group 146A.

*Petiole*.—Length: 18 mm. Diameter: 1 mm.

*Upper surface*.—Color: Greyed-Purple Group 183A.

*Lower surface*.—Color: Yellow-Green Group 146D.

*Rachis*.—Length: 20 mm. Upper surface: Color: Greyed-Purple Group 183A.

*Lower surface*.—Color: Yellow-Green Group 146D. Observations: Small prickles.

*Leaflet*.—Quantity: Normal number of leaflets per leaf in middle of the stem is 5 leaflets. Margins: Serrated. Size: Average size of the terminal leaflet on normal leaves is 22 mm in length by 11 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa,* downy mildew *Peronospora sparsa,* rust *Phragmidium* sps., black spot *Diplocarpon rosae,* and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Ground Cover rose class named 'Poultc021', substantially as illustrated and described herein, due to its abundant orange flowers, disease resistance, and extended period of bloom.

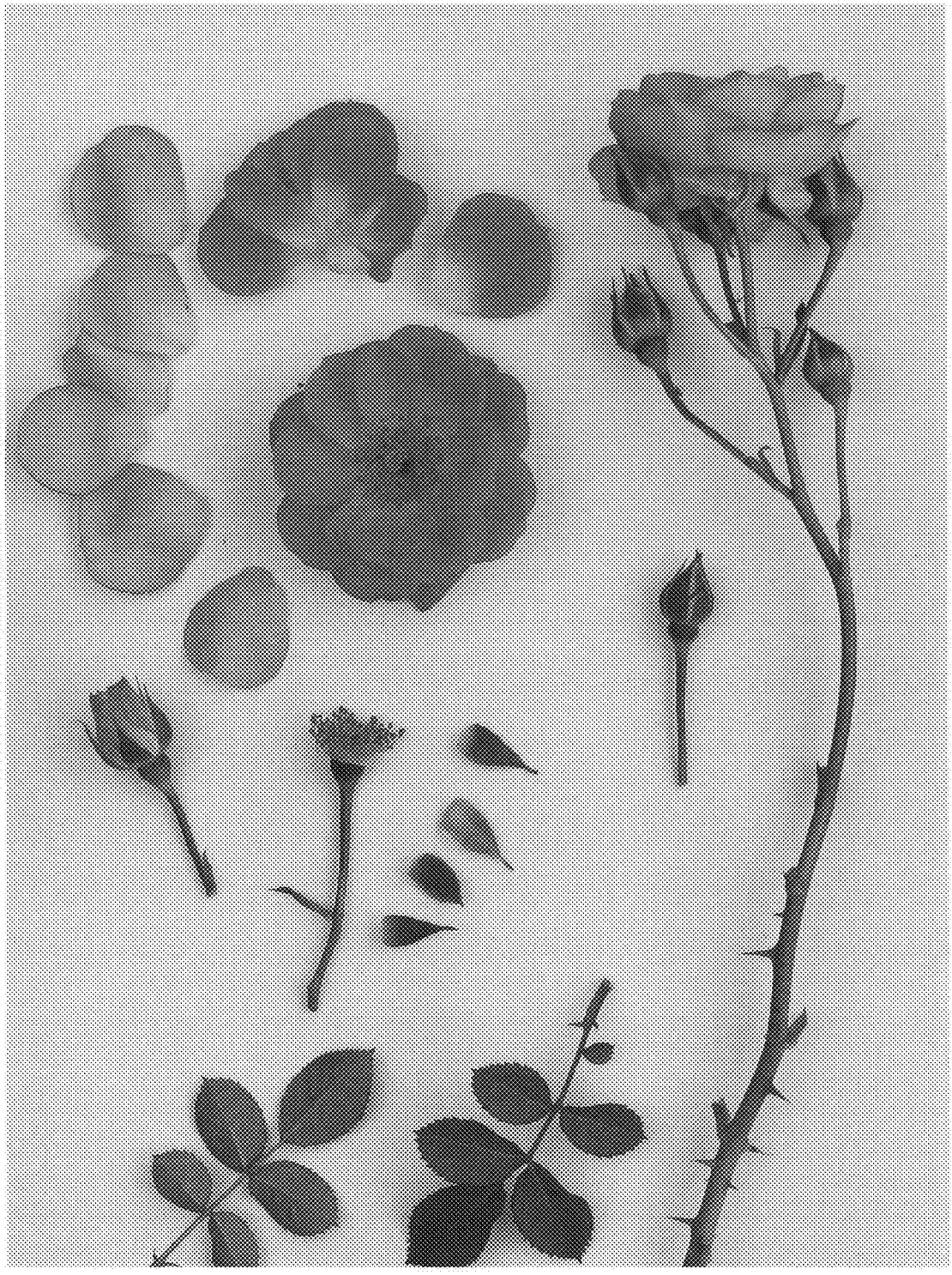

* * * * *